US009443010B1

(12) United States Patent
Sundeby et al.

(10) Patent No.: US 9,443,010 B1
(45) Date of Patent: Sep. 13, 2016

(54) METHOD AND APPARATUS TO PROVIDE AN IMPROVED VOICE OVER INTERNET PROTOCOL (VOIP) ENVIRONMENT

(75) Inventors: Bjorn A. Sundeby, Founex (CH); Kurt U. Lennartsson, San Jose, CA (US)

(73) Assignee: Glooip Sarl, Luxembourg (LU)

( * ) Notice: Subject to any disclaimer, the term of this patent is extended or adjusted under 35 U.S.C. 154(b) by 2133 days.

(21) Appl. No.: 11/864,539

(22) Filed: Sep. 28, 2007

(51) Int. Cl.
*G06F 17/30* (2006.01)
*G06K 9/00* (2006.01)
*G06F 19/00* (2011.01)

(52) U.S. Cl.
CPC ....... *G06F 17/30793* (2013.01); *G06F 19/327* (2013.01); *G06F 19/3418* (2013.01); *G06K 9/00677* (2013.01)

(58) Field of Classification Search
CPC ..................... G06F 17/30793; G06K 9/00221
USPC .............................. 370/356; 379/142.04, 249
See application file for complete search history.

(56) References Cited

U.S. PATENT DOCUMENTS

| 6,604,139 | B1 | | 8/2003 | Sajina et al. |
|---|---|---|---|---|
| 6,970,823 | B1 | | 11/2005 | Yago et al. |
| D533,562 | S | * | 12/2006 | Sundeby ...................... D14/490 |
| 7,461,258 | B2 | * | 12/2008 | Rolfe ............................ 713/176 |
| 8,374,324 | B2 | * | 2/2013 | Suryanarayana et al. ......................... 379/102.02 |
| 2002/0159571 | A1 | * | 10/2002 | Stock .......................... 379/88.02 |
| 2003/0058806 | A1 | * | 3/2003 | Meyerson et al. ............ 370/260 |
| 2006/0095262 | A1 | * | 5/2006 | Danieli ......................... 704/251 |
| 2006/0285659 | A1 | * | 12/2006 | Suryanarayana et al. . 379/88.02 |
| 2007/0041517 | A1 | * | 2/2007 | Clarke et al. ................ 379/67.1 |
| 2008/0033941 | A1 | * | 2/2008 | Parrish ............................. 707/6 |
| 2008/0123849 | A1 | * | 5/2008 | Samayamantry et al. .... 380/255 |
| 2008/0235724 | A1 | * | 9/2008 | Sassenscheidt et al. ....... 725/32 |
| 2008/0247529 | A1 | * | 10/2008 | Barton et al. ............. 379/211.01 |
| 2008/0247530 | A1 | * | 10/2008 | Barton et al. ............. 379/216.01 |
| 2010/0226261 | A1 | * | 9/2010 | Piche ............................ 370/252 |

OTHER PUBLICATIONS

Privacy Policy. HYPERNET. Jul. 25, 2006.*

\* cited by examiner

*Primary Examiner* — Parth Patel
(74) *Attorney, Agent, or Firm* — Blakely, Sokoloff, Taylor & Zafman LLP (57) ABSTRACT

A method and apparatus for an improved voice over Internet Protocol (VoIP) system is described.

21 Claims, 9 Drawing Sheets

METHOD AND APPARATUS TO PROVIDE AN IMPROVED VOICE OVER INTERNET PROTOCOL (VOIP) ENVIRONMENT

FIELD OF THE INVENTION

The present invention relates to VoIP, and more particularly to filtering of VoIP.

BACKGROUND

Many organizations and governments have the need of supervising what is said over they phone by employees in their organizations to guard against IP theft or guard against liability from saying the wrong thing or leaking confidential information. It is generally impractical to record all calls and analyze them. Furthermore, doing this means that the organization only becomes aware of a problem after it's too late.

Parents have the same problem. They want to give their children freedom by providing them access to a phone, and more frequently now an Internet connection, which enables the use of a PC phone (VoIP). There are many temptations for children that parents can foresee, but monitoring such use is difficult.

SUMMARY OF THE INVENTION

A method and apparatus for an improved voice over Internet Protocol (VoIP) system is described.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

The method and apparatus described includes a method of filtering data generated during a Voice over Internet Protocol (VoIP) session. In one embodiment, there are two distinctive filtering mechanisms that may be used alone or in combination, to solve the problems described above. One mechanism is filtering the voice stream itself, and the other is filtering the control protocol. In one embodiment, there may also be a pre-filtering for access. In one embodiment, if video or other image capabilities are included in the system, there may be an image-based pre-filtering. The pre-filtering may include in one embodiment a face recognition system to recognize the user at login time. The face recognition may be used to automatically log the user into the user's profile. The face recognition may, in one embodiment, be used for other filtering as well. For example, if a person's photo is on the public list of sex offenders the person can be identified and the session blocked as a protection measure in the community. For another example, known bad actors can be identified by image as well as by online identity, and blocked. This ensures that if a bad actor attempts to use a different ID, or borrow a friend's account, he or she can still be blocked successfully.

In one embodiment, content filtering may include threshold-based filtering. The threshold based filtering may use a library of reference material of offenders interactions/historical expressions. This data, in one embodiment, can be captured from evidence material in known cases and stored in the library. Then, when a set of similar phrases reaches a threshold it can trigger an alert. The alert may provide a notification, block the session, flag the possible offender's identity for review by an administrator, etc.

In one embodiment, the system may further provide the ability to utilize the VoIP phones to interact with users on instant messaging systems (IM). The system may provide pseudo-real-time text-to-audio and audio-to-text translation.

In one embodiment, the system may further provide translation between languages, if the VoIP users have different languages they can use.

Filtering the voice stream may include monitoring for vocabulary. The system may start recording when certain trigger words are identified. Trigger words may, for example include words such as "confidentiality," "cheating," or other appropriate words. In one embodiment, the system may provide a set of seed words, based on the client's needs. For example, trigger words for a corporation attempting to identify potential trade secret theft are different from trigger words for a parent attempting to ensure that a child does not discuss taking drugs. In one embodiment, the system may provide blocking by keyword as well. In one embodiment, the blocking may be based on a cumulative set of words, as compared to a library. The library may include language examples for various triggering topics, such as drug use, sex offenders, etc.

This blocking may be pseudo-real-time. That is, it may occur sufficiently quickly to be undetectable by the listener. In one embodiment, blocking may include: disconnecting the conversation when the keyword is detected, beeping or replacing the keyword, or otherwise blocking the conversation when the trigger word is detected.

In one embodiment, the filtering system may further include language recognition. In one embodiment, the system may provide filtering of vocabulary in different languages, and recognizing certain words in any language may trigger recording of the session. In one embodiment, the same system may provide pseudo-real-time translation between languages.

Filtering the destination may include filtering by phone number, number block, and number type. In one embodiment, the system may provide a category of numbers that are blocked. For example, many companies and families may wish to block 1-900 numbers, which tend to be affiliated with pay-by-the-minute services. In one embodiment, users may selectively unblock individual numbers within a blocked category. Individual numbers may be blocked. In one embodiment, an administrator or authorized user may review the caller-ID listing and easily block numbers from there. In one embodiment, other criteria for blocking numbers may be used. Some of these criteria may include: cost per minute, destination country, destination company, etc.

In one embodiment, the system may add time-based limitations to the blocking. For example, in one embodiment, certain numbers cannot be reached at certain hours. For example, in a corporate environment, calling a competitor after hours may be an indication of a problem. For example, calls may be filtered based on time of day. For example no calls will be allowed after 10 at night for incoming and outgoing depending again on filter settings, or no calls may be over 30 minutes. Or potentially a combination of such criteria as time of day (time of week, time of year, etc.), and length.

In one embodiment, the filtering may further be based on approved criteria in the control signaling protocol such as incoming or outgoing phone numbers, names services etc. In one embodiment, the Session Initiation Protocol (hereinafter "SIP protocol") is used. The SIP protocol is a text based protocol which is easy to decode.

Filtering in one embodiment includes filtering based on voice recognition. The system may initiate recording or blocking when a certain voice is recognized, the caller, the recipient, or both. In one embodiment, the voice recognition may require recognition of both voices, i.e. the caller and the recipient.

The system may further provide authentication of calls based on caller recognition. In one embodiment, the voice recognition may be used for billing purposes, as well as to control/provide access. For example, in one embodiment, only a recognized user who has authorization may make long distance calls. In one embodiment, this also permits flexible workspace, where any user can sit at any desk. By using voice recognition, the system can display/send user name to any other VoIP, regardless of where the user is seated. Furthermore, the telephone system may be automatically configured with the user's settings, based on the voice recognition. In one embodiment, similar features may be provided using video images for a VoIP system which includes video. Thus, instead of voice recognition, face recognition may be used for log-in, authentication, and filtering.

In one embodiment, the filtering may include filtering based on ports and application properties. In one embodiment, the system uses a firewall-based filtering technology activated by filtering for VoIP applications based on known ports and application properties such as application name. For example, the system may permit the use only of a particular VoIP application, while others are prohibited.

In one embodiment, the system may further include additional filtering based on other settings or criteria. In one embodiment, filtering criteria and settings may be controlled by an authorized user. In a family environment, this may be the parent. In a corporate environment, this may be one or more authorized users within the Human Resources, Security, or other appropriate department. In one embodiment, the filter criteria and settings may be adjusted through a web site.

Figure 1:
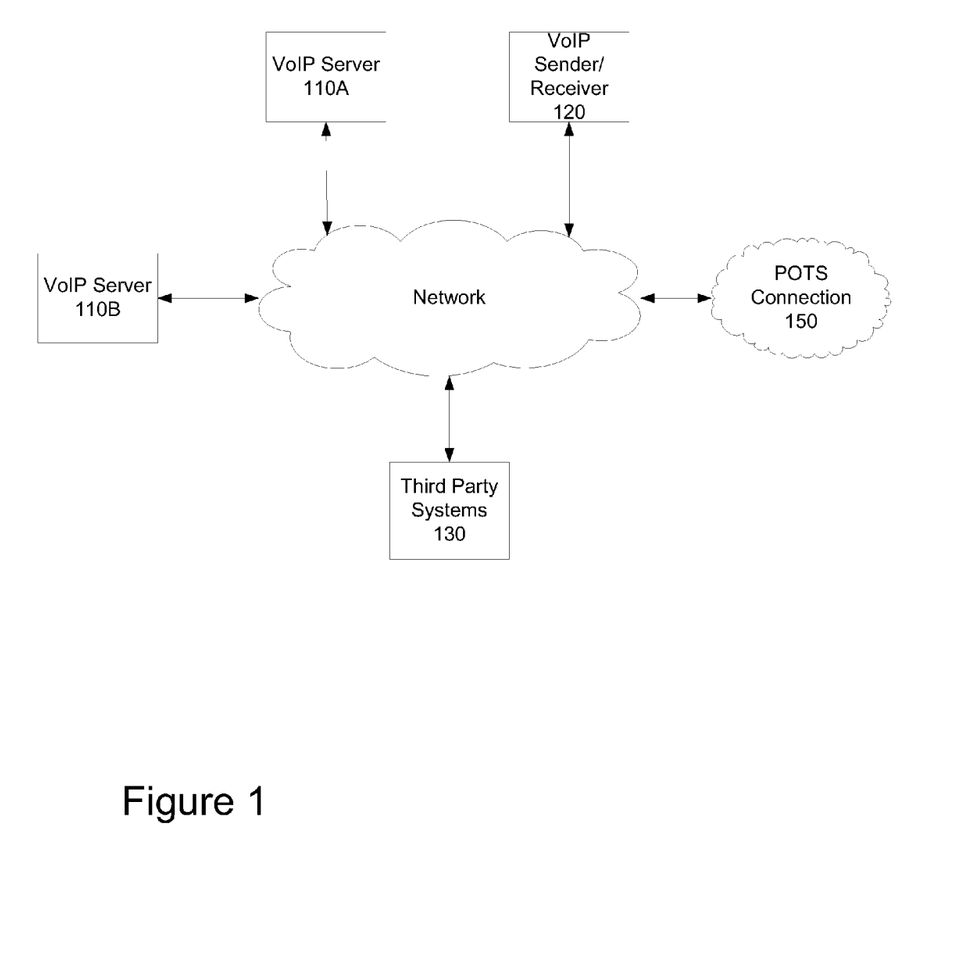
FIG. 1 is a block diagram of one embodiment of a network on which the present invention may operate.

FIG. 1 is a block diagram of one embodiment of a network on which the present invention may operate. The system includes a VoIP server 110 in accordance with the present invention. A plurality of VoIP sender/receiver systems 120 may be coupled to the server 110. In one embodiment, the server may be behind a firewall of a corporation. In one embodiment, the VoIP sender/receiver systems 120 may be remote systems. The network further connects to third party VoIP systems 130. The present VoIP system is capable of interface with third party systems. However, as described below, in one embodiment certain of the features are not available when the connection is initiated or terminated outside the VoIP system 110, 120. In one embodiment, there may be multiple VoIP servers 110. These servers may be designed to serve different clients. In one embodiment, special features are available for connections between VoIP systems 110A, 110B implementing the architecture of the present invention. In one embodiment, the VoIP system can interface with conventional Plain Old Telephone Service (POTS) connection, via POTS connection 150.

Figure 2:
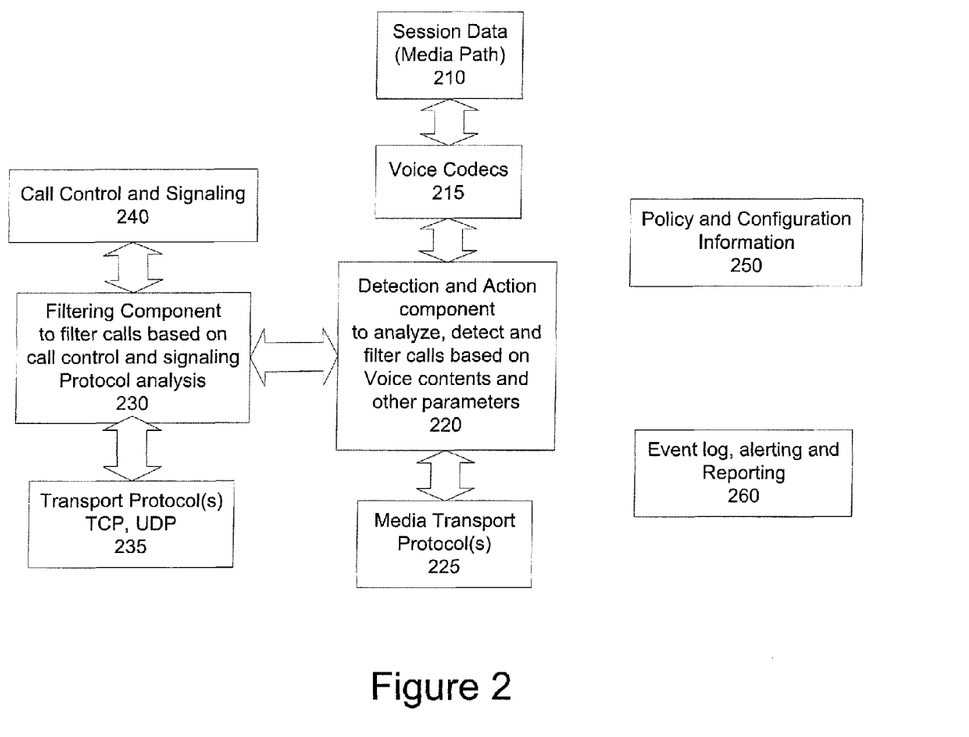
FIG. 2 is a block diagram of the high-level architecture of the VoIP system including filtering.

FIG. 2 is a block diagram of the high-level architecture of the VoIP system including filtering. The Policy and Configuration Information (PACI) block 250 is responsible for maintaining policy and configuration information. In one embodiment, the policy and configuration information is received, or downloaded, from the central server. In one embodiment, the PACI block 250 receives data via a secured link from the server. In one embodiment, the PACI block 250 stores the policy and configuration information in a secure manner.

VoIP applications have two distinct elements one for call control and signaling 240 and the other for session data 210. The call control and signaling 240 is responsible for call setup and management. The session data 210 path carries packetized data between the end-points. Generally, the data is voice data. In one embodiment, the data may include voice and video data. Because of this, in one embodiment, the architecture above divides the functionality in different sub-modules as shown above.

A filtering component 230 sits between Call Control and Signaling 240 and the corresponding transport protocols (TCP/UDP) 235. The filtering component 230, in one embodiment, is responsible for monitoring and blocking calls to and from blocked phone numbers/addresses. The filtering component 230, in one embodiment, is also responsible for selectively allowing or blocking certain VoIP applications to establish calls and enforce time restrictions as per the policy information.

The Detection and action component (DAC) 220 monitors the session (media) data to enforce the policy. In one embodiment, the DAC 220 monitors, analyzes and controls the packetized voice and video data when available, controls the session, and triggers actions. These actions may include one or more of the following: filtering prohibited words, authenticating user, triggering monitoring of the call based on the voice recognition and/or contents, and cumulative filtering/triggering. In one embodiment, the DAC 220 can also interact with other modules to force disconnection of the call to enforce the policy.

In one embodiment, the voice signals are tapped directly from the audio devices i.e. before the microphone signal is fed to the codec and before the codec output is fed to the speaker. However, considering the architectural and platform specific differences, this may not be always easy and feasible task for all popular $3^{rd}$ party VoIP applications. Therefore, in one embodiment, the system is capable of tapping the encoded voice data, and processing it for detection.

The DAC 220 in one embodiment provides sophisticated rule processing capabilities. DAC 220, in one embodiment, is capable of building and maintaining updated context for a conversation/session. The detection rules could be as simple as filter/record/alert a session on finding an occurrence of a specific word or a phrase. However to make the detection more effective and robust, in one embodiment the DAC 220 engine is capable of processing more complex rules which can make use of context. The rules and corresponding actions may be defined based on a number of parameters. These parameters, in one embodiment, may include one or more of the following: direction of word/phrase usage (i.e., use of word/phrase in a specific context could be allowed but not otherwise), ability to assign weight and/or threshold to occurrence of certain words/phrases, combination and sequence of words etc.; logical combination (AND and OR) of the above rules.

In one embodiment, there may be a library of phrases/words/contexts which may be used by the system for this detection process. The library, in one embodiment, may include company-specific terms. In one embodiment, the library may include phrases and language gleaned from data about sex offenders. In one embodiment, the library may include text from prior conversations or instant messenger communications which have been flagged as indicating a problem, which makes filtering appropriate.

The Event log, alerting and Reporting EAR module 260 is responsible for logging any events and reporting them to the central database for monitoring and reporting. In one embodiment, the EAR module 260 logs events that trigger any filtering action. In one embodiment, other events may be logged as well.

Figure 3:
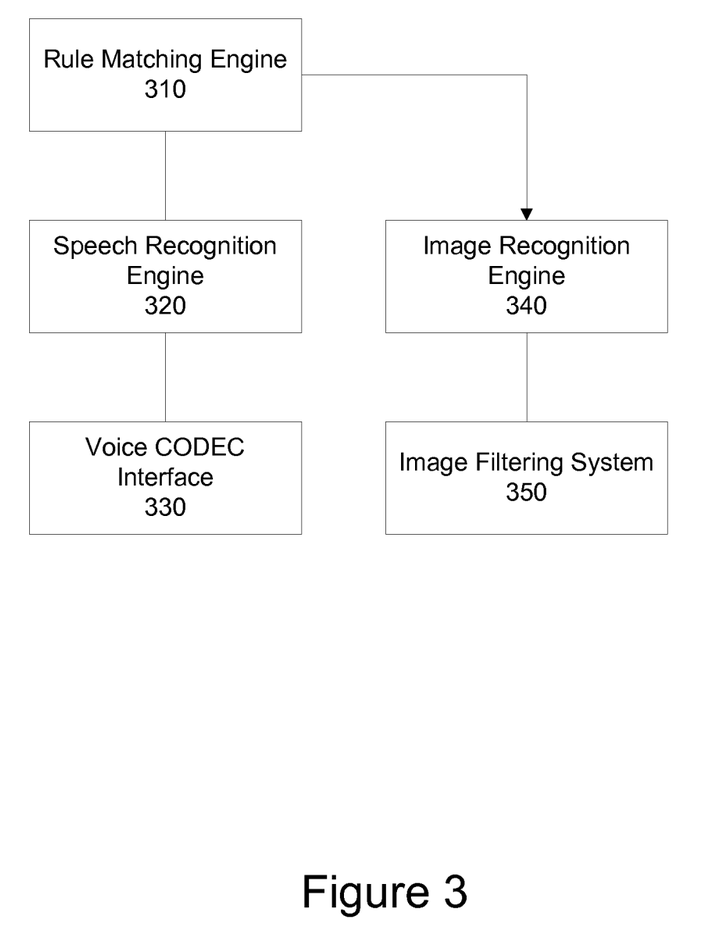
FIG. 3 is a block diagram of one embodiment of the Detection and Action component of the system.

FIG. 3 is a block diagram of one embodiment of the Detection and Action component of the system. In one embodiment, the DAC 220 in the media path is structured into three layers each having distinct functionality and interface with the other layers.

The bottom layer 330 interfaces with voice codecs to tap the audio signal (in one embodiment raw) and provides a consistent interface for the upper layers. In one embodiment, the bottom layer 330 provides an interface for all of the available various codecs and any platform specific differences as well.

In one embodiment, a parallel bottom layer for image and/or video data captures the data and provides it in a consistent form to the upper layers.

The middle audio layer 320 is responsible for speech recognition. The middle layer 320 interfaces with the voice codec interface layer (bottom layer 330) to tap into the audio signal and with the rule matching engine for advanced rule matching capabilities. In one embodiment, the middle layer 320 is highly platform specific as far as speech recognition is concerned. For example, in certain implementations on Microsoft platforms the speech recognition may be based on Speech Application Programming Interface (SAPI), while other implementations could use APIs specific to other speech recognition engines along with related grammar and vocabulary. The middle layer 320 in one embodiment also includes a call control layer for call state information and call control etc. The call control layer interfaces with the upper layer 310 to report the results of recognition as the conversation progresses.

In one embodiment, the speech recognition engine 320 also provides a translation mechanism, to ensure that words are recognized regardless of which language they are spoken. In one embodiment, the translation mechanism has a limited set of available languages. In one embodiment, the translation mechanism, in addition to being used for matching, can be used for providing mechanical translation during conversations. Therefore, in one embodiment, the translation is pseudo-real-time.

The middle video/image layer 340 provides image based filtering and face recognition. Face recognition utilizes the video or still image of the user's face for biometric identification. The face recognition tool can also be used for filtering. For example, a parent may prohibit contact between his or her child and a particular bad influence. Regardless of what number/ID the caller is using, the face recognition engine can be used to identify the person. Similarly, face recognition engine can be used to match face data to a database of sex offenders, or other banned individuals.

The upper layer 310 rule matching engine is responsible for matching complex rules specified by the policy configured by the user(s). The upper layer 310 is also responsible for building and maintaining conversation context, and the DAC 220 uses this context in rule matching (depending on the rule). The authorized users and/or administrators for an organization can create complex rules via a user interface. In one embodiment, the user interface is a web based interface. The rule matching engine upper layer 310 takes recognition results from the speech recognition engine and processes rules e.g. detection of certain words/phrases along with corresponding weights, number of occurrences, direction of conversation etc. In one embodiment, the rule matching engine upper layer 310 takes image/video data and applies the rules as defined. Below are some examples:

a) A rule could trigger and take configured action if certain bad/prohibited words are detected in a conversation. For this purpose, in on embodiment, the weight assigned to the bad/prohibited words is a maximum.

b) If in a conversation the combined weight of a set of detected words/phrases over a period of time exceeds the configured threshold then a rule will be triggered. This could be helpful in detecting and controlling different types of conversations which may result liability or bad behavior, such as abusive, violent, racist, sexually inappropriate, etc.

c) A conversation may be compared to a set of communications by bad actors, for example sex offenders, and if the similarity match is identified, a rule could be triggered.

The Rule Matching Engine upper layer 310 interfaces with the lower layers 320, 330, 340, 350 as well as the call control module to initiate configured actions when one or more rules are triggered by the contents of conversation or video data. Example actions include i) terminate the call ii) record the conversation (subject to legal provisions), iii) mask certain parts of the conversation, iv) alert a designated individual, etc.

Figure 6:
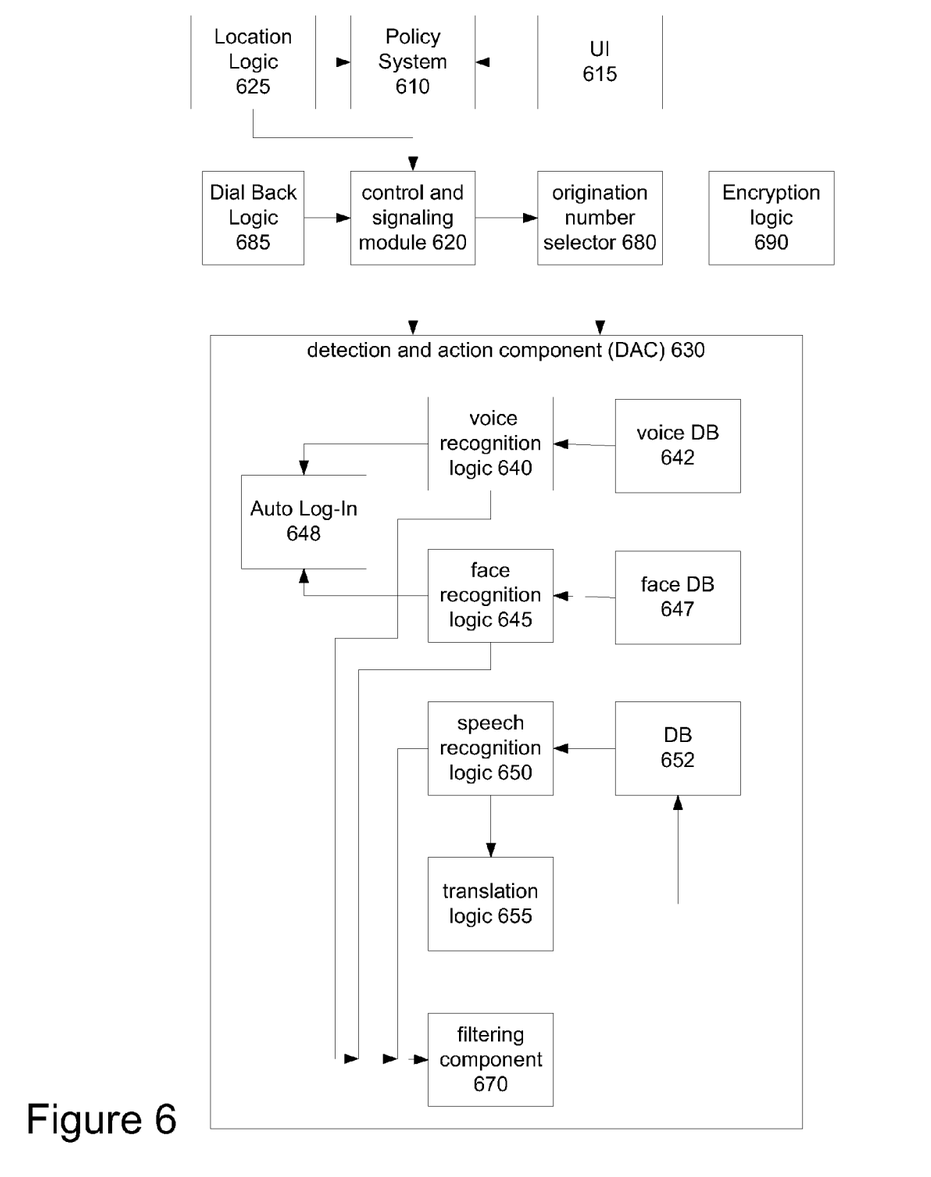
FIG. 6 is a block diagram of one embodiment of the system.

FIG. 6 is a block diagram of one embodiment of the system. The system 600 includes a policy system 610 to store one or more rules. The rules define the requirements for establishing and terminating a connection, the various filters that are available, etc. Policy system 610 enables an authorized user to add or modify rules through user interface 615.

The system includes a call control and signaling module 620 to set up the connection, and terminate connections.

In one embodiment, location logic 625 receives location data from a GPS device on the user's system, network triangulation, or another means to obtain location data. This location data is passed on, in one embodiment to the policy system 610. At certain locations user ID and password may be sufficient—for example, at known locations (for example the location where the user registered, at work or similar known locations). At other locations, additional authentication methods may be required by the policy logic 610.

Figure 8:
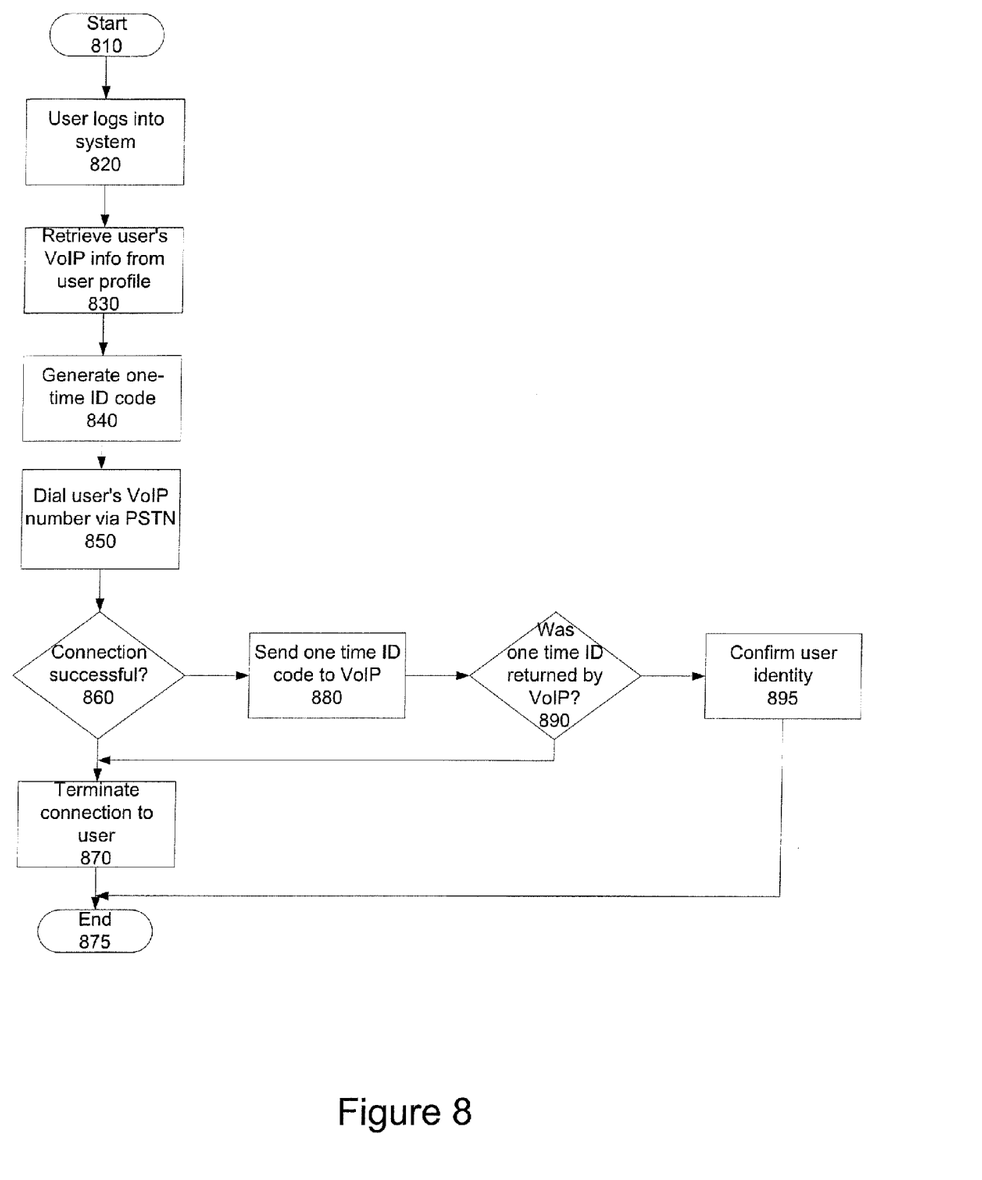
FIG. 8 is a flowchart of one embodiment of the server perspective of using dial-back security.
Figure 9:
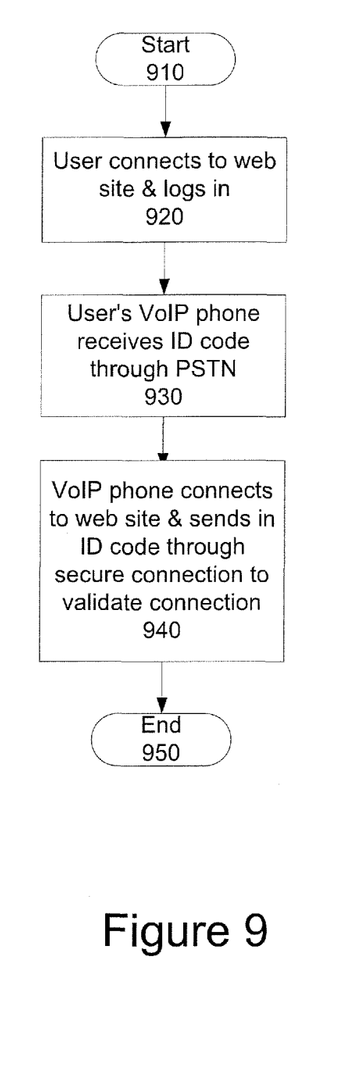
FIG. 9 is a flowchart of one embodiment of a client perspective of using dial-back security.
Figure 10:
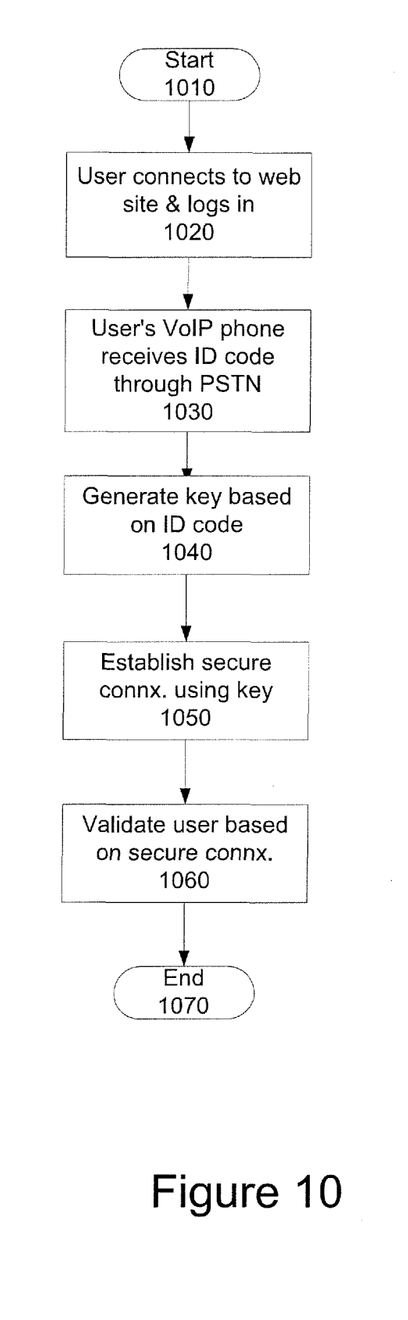
FIG. 10 is a flowchart of another embodiment of a client perspective of using dial-back security.

In one embodiment, dial back logic 685 is used to ensure that the user's VoIP identity matches reality. In one embodiment, dial back logic 685 includes a security logic to generate a one-time ID and to send the one-time ID to a user's VoIP system via a PSTN, a monitoring logic to monitor a return of the one-time ID through a network connection, and a notification logic to notify the call control and signaling module to terminate the connection when the one-time ID is not received. FIGS. 8-10 below describe the functionality of the dial back logic 685.

The call control and signaling module 620, in one embodiment, receives authorization from a detection and action component (DAC) 630, for establishing and maintaining the connection. The DAC 630 is designed to monitor a data stream of the connection, and detect when the connection meets the rule. The call control and signaling module 620 may, in one embodiment, provide filtering based on a connection identifier.

In one embodiment, the DAC 630 includes voice recognition logic 640 to recognize a voice. This enables the use of rules based on the identity of a call originator, a call recipient, or both. In one embodiment, the DAC 630 includes face recognition logic 645, to recognize a face. Like voice, recognizing a face enables various filtering and screening techniques. In one embodiment, the face may be matched to a database of face data of known bad actors. For a child user, the known bad actors may include registered sex offenders, while in a corporate setting known bad actors may include private investigators, competitors, and/or some other known problems.

Face and/or voice matching may be done automatically for log-in as well, enabling a user to log into the system easily. Auto log-in logic 648 may use this data to automatically provide access at the appropriate level to the user. In one embodiment, the face/voice matching is done automatically when audio/image data becomes available.

In one embodiment, the system includes speech recognition logic 650. Speech recognition logic 650 identifies words in the conversation. In one embodiment, speech recognition logic 650 is used to identify words, phrases, and/or contexts in a conversation. This enables the system to enforce a rules based on words, phrases, or context. Context may include a series of words in sequence, or a preponderance of certain trigger words, etc. The trigger words may include a series of words. In one embodiment, the trigger word includes a plurality of weighted words, the combination of weighted words indicating that the rule has been met.

In one embodiment, translation logic 655 is coupled to speech recognition logic 650. As is known in the art, pseudo-real-time translation can be performed based on words, or phrases. The system may perform one or both. In one embodiment, the language being used is automatically detected. In another embodiment, the user selects the original language and the destination language to which the system should translate. In one embodiment, the translation logic 655 may also be used to ensure that forbidden topics/words/subjects are not discussed in another language either. Thus, for example, in a student environment, the word "cheating" surrounded by the appropriate context, can be detected in a variety of languages. This ensures that the filtering cannot be evaded simply by switching languages.

The system may further include a filtering component 670 to perform an action when the connection meets the rule. The action may include translating the voice data, logging-in a user, terminating a call, turning on call monitoring, beeping out certain words, etc.

The system may further include an origination number selector 680. In one embodiment, the user may select one of a plurality of numbers as the originating number. Each of those numbers is linked to the same destination address. For example, a user may have a VoIP number which includes a series of numbers ranging from 0 to 9 as the last digit. The user may, via number selector 680, select the origination number.

Filtering component 670 may then be used to set rules for calls based on the number being called. For example, a user may set the last-digit-0 number as the base number. However, the user may always utilize the last-digit-9 number for telephone calls directed to business partners. In that case, the user may set up rules for all incoming calls directed to the last-digit-9 number. For example, it may go into a special voicemail box, with a separate announcement.

In one embodiment, the system may further include encryption logic 690. Encryption logic 690 secures certain communications between the parties. In one embodiment, a hyper sign, described in more detail below, is used to establish a secured connection.

In one embodiment, the user's system may include a GPS (global position system) receiver. The server may, in one embodiment, include location based services 605. In one embodiment, the user's system may include a GPS (global position system) receiver. The server may, in one embodiment, include location based services 605. The user's phone provides GPS data to the server. The location based services 605 in the server can provide information regarding local providers advertisers for such things as restaurants, gas stations, barber shops, etc. In one embodiment, since the advertising connects to the VoIP phone, the user can call by double clicking on the ad or the list presented in the client.

In one embodiment, when a user calls an emergency number—911 (US) or 112 (in Europe)—the location based services 605 uses the GPS data to determine the user's location. The location bases services 605 in one embodiment has a routing list for emergency contacts around the world. In one embodiment, the emergency contracts may be dispatch services for a local area. In one embodiment, emergency contacts may include the user's preset contracts. The location based services 605 in one embodiment will dial the closest service and send a voice message with the location as soon as someone picks up the phone. In one embodiment, the location based services may send and an email and SMS like message for centers that support that type of additional information.

The above processes may be provided on the server side, on the client side, or split between the client and the server.

Figure 4:
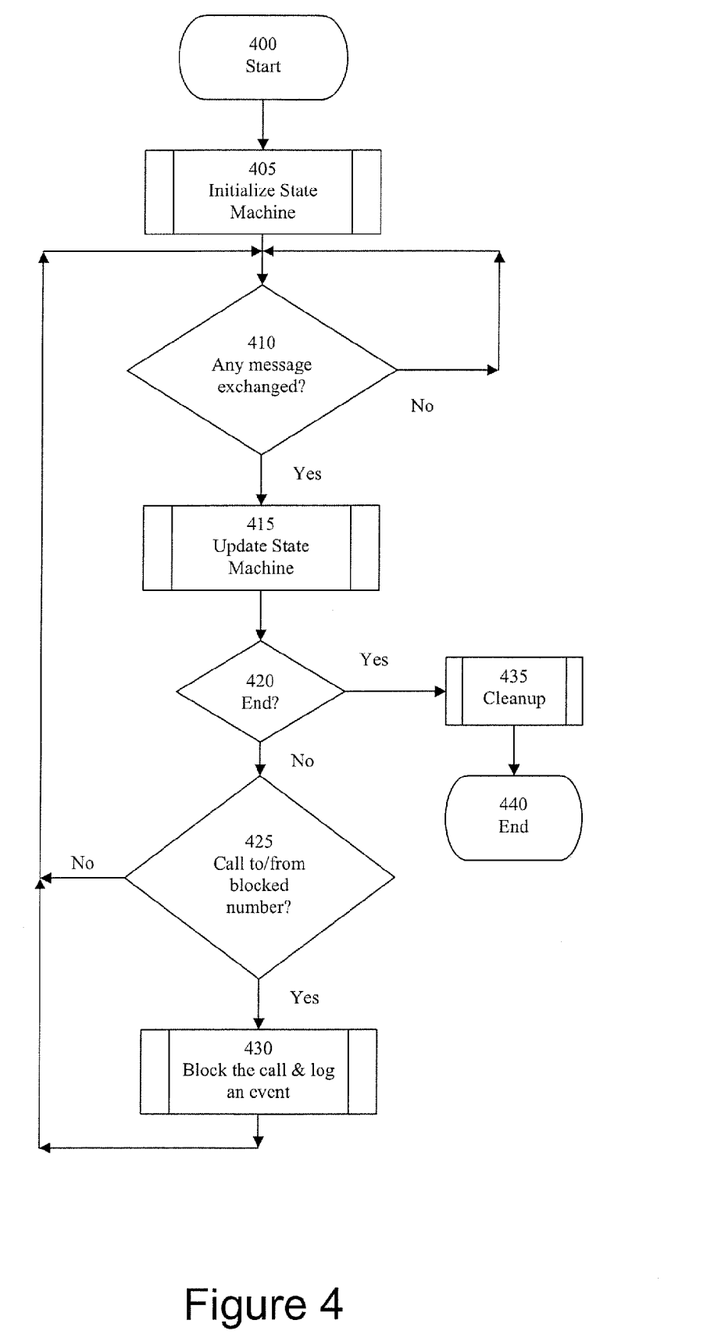
FIG. 4 is a flowchart of one embodiment of the rule matching engine's functioning.

FIG. 4 is a flowchart of one embodiment of the rule matching engine's functionality. The Rule Matching process starts at block 400 when a new call is established (matured). In one embodiment, only certain calls may be subject to this type of monitoring. In that case, the process starts when the designated call type is established. At block 405 the process initializes a context for the call to hold all the dynamic (state) information throughout the progress of the call. The process then continues to block 410 where it checks if the call has ended. If yes, the process proceeds to block 450 where the context is cleared and the processes ends at block 455. If not, the process proceeds to 415 to check if any result/data is available from the Recognition Engine (RE). The recognition engine may include a speech recognition engine and an image/video recognition engine.

If no result/data is available at block 415, the process returns to block 410 to determine if the call has ended, and then to return to monitoring. If some data/recognition result is available from the SRE, the process continues to block 420 to process the data and match rules.

At block 420 the process determines if one or more rules are matched in the word/phrase/context/video/image reported by the RE. If not, the process returns to block 410.

If one or more rules are triggered based on the word/phrase/image/video/context reported by the RE, the process continues to matching of those rules in 425.

At block 425, in one embodiment, the process determines if the direction of the detected word/phrase matches the direction configured in the rule(s). If the direction does not match, the data is ignored and the process returns to block 410. Note that the previous data is not discarded from the RE, in one embodiment. Therefore, this evaluation is cumulative. In one embodiment, only certain sets of words/phrases images have directionality. This step is only performed for those sets. Otherwise, the process continues directly to block 430.

If the direction matches, the process continues to block 430 where the context is updated for each applicable rule for which the detection result (i.e. word/phrase) is applicable. More specifically the following attributes are updated in one embodiment:

1) Update the weight information based on the configured weight for the word/phrase/image/video/context detected. E.g. abusive words could be assigned very high weight so that even a single occurrence could be enough to trigger a rule,
2) Update the occurrence count
3) Time Stamp
4) Sequence No. (ID)—(this can be useful in triggering rule(s) if certain words occur in certain order or context).

The process then continues to block 435 where the process checks the updated context to see whether an action should be triggered. In one embodiment, the process tests for certain conditions (based on the configuration). Exemplary conditions may include:

1) Combined weight of all detected words/phrases exceeds the configured threshold?
2) Number of occurrences over a period of time exceeds certain limit?
3) Are certain words spoken in some specific order?

More complicated rules can be defined using the basic constructs explained above and logical operators AND and OR etc.

At block 435, detection results are processed and checks are made to see if any one or more of the configured rules are triggered. If no rule matches, the process returns to block 410 to continue monitoring. If one or more rules match, the configured actions are initiated, at block 440 (e.g. terminate or record call etc.). The process then logs the event alert with the details at block 445. The process then returns to block 410. As part of the configured action, if the call is terminated, the process will then go to block 450 to clear the context and processing ends at 455.

Figure 5:
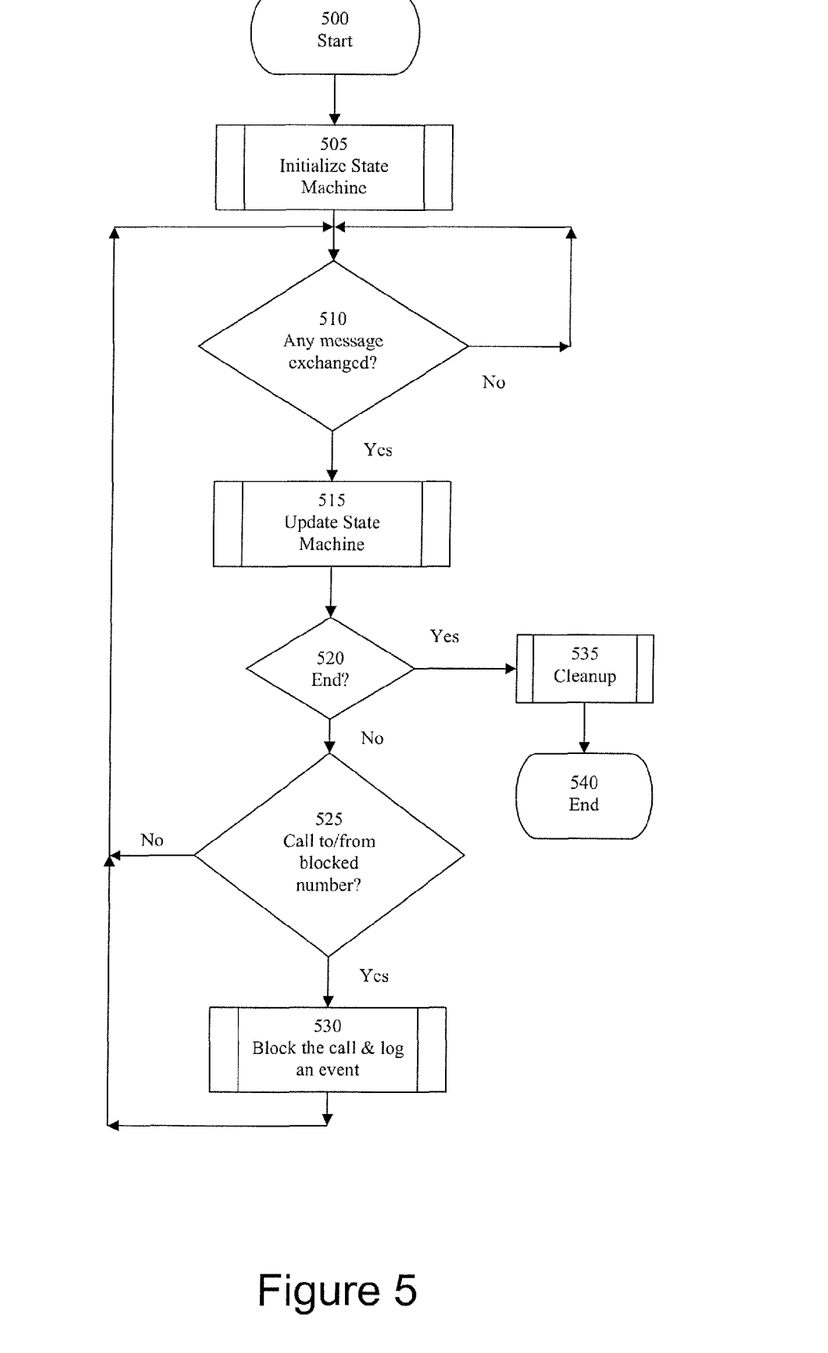
FIG. 5 is a flowchart of one embodiment of control channel filtering.

FIG. 5 is a flowchart of one embodiment of control channel filtering. As explained earlier, the control channel filter component sits between Call Control and Signaling applications and the corresponding transport protocols (TCP/UDP). The control channel filter is responsible for monitoring and blocking calls to and from blocked phone numbers/addresses.

The process starts at block 500 and at block 505 it initializes the state machines for call setup and management protocols. The process is capable of monitoring multiple different protocols and in one embodiment it has independent state machines for this purpose. The process then proceeds to block 510 to check if any call control (e.g. call setup or call management) message has been exchanged. It will remain in this state until a message exchange is detected.

If a message exchange is detected, the process continues to block 515 where the message is decoded and the state machine is updated. Next, at block 520 the process determines if the state machine has terminated its process as a result of the last exchanged message. If yes, the process performs necessary cleanup at block 535 and ends at block 540. Otherwise, the process continues to 525 where a check is made on the type of message exchanged and the other details. If the message is related to call setup, checks are made on the called/calling number and the current time. If the called/calling number is blocked by the configured policy or if the current time is beyond the permitted time window specified by the configured policy then the call is blocked and an event is logged. An appropriate response message is be generated and state machine is updated. The process then returns back to block 510 and wait for further messages.

Figure 7:
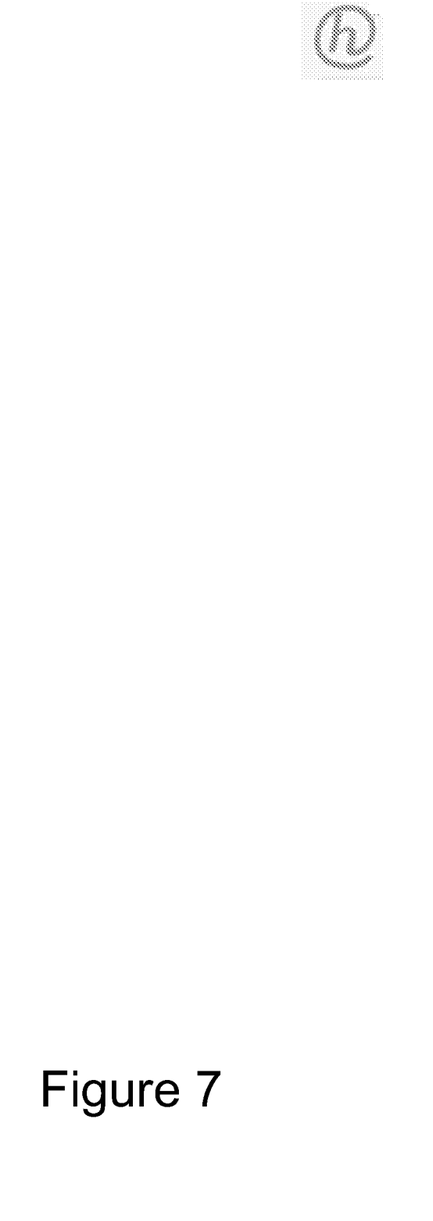
FIG. 7 is an exemplary illustration of a hyper-symbol which may be used.

In one embodiment, the filtering system described herein further provides call privacy. In one embodiment, calls between system users are automatically encrypted and authenticated for confidentiality, integrity and replay protection. In one embodiment, a special signal—referred to as a hyper sign—is used to indicate that the call is encrypted. In one embodiment, the sign is a hyper sign (special formatted h similar to @) is used. FIG. 7 illustrates an exemplary hyper sign which may be used. Typical SIP addresses use a format similar to email e.g. sip:user1@hypernet.com. Instead of @, system users can use the hyper sign for SIP addresses of other system users to automatically ensure call privacy. The control channel processing module will look for the hyper sign in the address. Whenever a call is being established to SIP address with hyper sign (instead of the @), the control channel will automatically use secure protocols (in one embodiment Secure Real-Time Transport Protocol (SRTP)) for the media (voice) path.

In one embodiment, if a SIP address uses the normal @ sign, i.e. the call is to outside the system, call privacy settings will not be applied automatically. This will ensure interoperability with other users and standard phones.

In one embodiment, the system enables the use of a call interruption indicator. In standards based VoIP systems, call management i.e. control message exchange, happens over TCP based protocols (e.g. SIP) whereas the voice data is carried by transport protocols (e.g. RTP) that uses UDP. While this works well for carrying data that is highly sensitive to delays it is susceptible to packet loss.

Because of transient problems in the Internet, sometimes it happens that the voice path (in one or both directions) gets disrupted without immediate knowledge of the user(s). This results in the person continuing to talk for a long time only to realize later that the other person is unable to hear the conversation. Besides the inefficiency, this can cause confusion and frustration among the users.

Call interruption indicator implements a monitoring mechanism that is non-intrusive and transparent to the users and can warn the user when the other user is unable to hear the conversation. In one embodiment of the system, the call interruption indicator is based on the delivery monitoring capabilities of underlying more modern RTP protocol based on TCP instead of UDP. In another embodiment of the system, it is implemented by periodically sending specially crafted voice data packets and monitoring the response. The recipient client handles the packet in a specific manner and responds much like echo request-response mechanism used in some popular applications e.g. the ping utility.

The sender application keeps track of sent requests and monitors the responses. If appropriate response is not received for certain number of attempts within certain period of time the application indicates the user about a potential problem. This feature works when both the clients involved in a conversation are compliant software clients. The indication may be an audible indicator or a visual indicator, when the connection has been interrupted. This ensures that the user becomes aware that the connection has become unstable. The user may then disconnect from the conversation, wait until the connection is successfully reestablished, or react in other ways. In one embodiment, the sender application monitors the connection quality continuously. In one embodiment, connection quality data is logged. This data may be used to evaluate the VoIP system, as well as alerting administrators to recurring or systemic problems.

FIG. 8 is a flowchart of one embodiment of the server perspective of using dial-back security. The flowchart starts at block 810. In one embodiment, this process starts when the application is initiated. In one embodiment, the process starts at block 820, when a registered user logs into the system.

At block 830, the user's VoIP information of the user is retrieved. This information can be found in the user's registration profile.

At block 840, a one-time ID code is generated by the system. In one embodiment, a security logic generates the one-time code.

At block 850, the user's VoIP number is dialed. This is done, in one embodiment, using conventional PSTN (Public Switched Telephone Network). The PSTN attempts to establish a connection with the known VoIP telephone number of the user.

At block 860, the process determines whether the connection was successful. In one embodiment, the process attempts to establish a connection until either the connection is established, a set number of attempts have been unsuccessful, a set period has elapsed, a particular error message is received, or another predetermined event occurs.

If the connection was not successful, at block 860, the user's connection to the system is terminated, at block 870. In one embodiment, if a connection is terminated a flag is set in the system to indicate that this account may be compromised. In one embodiment, a notification may be sent to the email address of the user, accessible outside the system. In one embodiment, after a preset number of connection terminations, a manual re-activation of the account is required. The process then ends at block 875.

If, on the other hand, a connection was successfully established, at block 860, the process continues to block 880. At block 880, the one-time ID code generated above is sent to the user's VoIP number.

At block 890, the process determines whether the user's system returned the one-time code via the network connection established by the user, when the user logged into the system (block 820). In one embodiment, the system waits for a predetermined time before determining that the code was not successfully returned. In one embodiment, during the validation process, the user may have limited access to the system. In one embodiment, the user may browse but may not see other users' personal information, or any information that is deemed secure information (for example the user's contact lists). In another embodiment, the user may not be provided any access during this process. In another embodiment, the user may be provided full access during this time.

If the one-time ID was returned, at block 895 the user's identity is confirmed. The user can then enjoy full access to the system. The verification process then ends. If the one-time ID was not returned, the process continues to block 870, and the user's connection to the system is terminated.

This process provides a two-path validation of the user by sending data through the PSTN. Therefore, in order to impersonate a user a hacker would have to hack the PSTN in addition to the user's own system. In one embodiment, this process is run every time the user logs into the system. In another embodiment, this process is run randomly, but not every time the user logs into the system. In one embodiment, this process is run randomly, and independently of the user logging into the system. In that embodiment, the process may randomly test one of the connected user's, regardless of whether the user has just logged into the system or has been connected for some time.

FIG. 9 is a flowchart of one embodiment of a client perspective of using dial-back security. The process starts at block 910. The user connects to the web site and logs in, at block 920. At block 930, the user's VoIP phone receives a one time ID code through the PSTN. This may be done through any conventional mechanism.

At block 940, the VoIP phone connects to the web site, via the user's established connection with the site, and sends the ID code through the secure connection. The code is then used to validate the user. In one embodiment, the VoIP phone may have special software to handle this process. In one embodiment, the ID code is sent with instructions designed for the VoIP phone. Therefore, in one embodiment, a conventional VoIP system set-up may be used with the system. The process then ends at block 950.

FIG. 10 is a flowchart of another embodiment of a client perspective of using dial-back security. The process starts at block 1010. The user connects to the web site and logs in, at block 1020. At block 1030, the user's VoIP phone receives a one time ID code through the PSTN. This may be done through any conventional mechanism.

At block 1040, a key is generated from the one time ID. In one embodiment, the key may be generated through a one-way hash function.

At block 1050, a secure connection is established with the website using the key. The web site also knows the one time code. In one embodiment, the secure connection may be a conventional connection with all data encrypted by the key. In another embodiment, the connection may be an SSL connection.

At block 1060, the secure connection is used to validate the user. In one embodiment, the server may send the user's VoIP phone some special software to enable this process. In one embodiment, this occurs when the user initially signs up to the system. In another embodiment, the VoIP client software may be downloaded from the server, and may include this security functionality. The process then ends at block 1070.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:
1. A voice-over-internet protocol (VoIP) system comprising:
    a policy system to store a plurality of classifications to identify a plurality of types of VoIP connections, a type of the VoIP connection having an associated rule;

a call control and signaling module to set up the VoIP connection for a user of the VoIP system;

a filtering component to determine whether the VoIP connection is of a high risk type based on at least one of the plurality of the classifications, the determination being performed by the filtering component in response to the VoIP connection being set up for the user;

a detection and action component to monitor a data stream of the VoIP connection, the monitoring being performed by the detection and action component in response to the determination that the VoIP connection is of the high risk type and the detection and action component to detect when the VoIP connection violates the associated rule;

a biometric logic to compare one or more biometrics of the user of the VoIP system to one or more biometrics of known bad actors in a biometric database having biometrics of the known bad actors, the comparison being performed by the biometric logic in response to the determination that the VoIP connection is of the high risk type and without regard to any username, telephone number, user address, Session Initiation Protocol (SIP) address, or VoIP number that is associated with the VoIP connection, the associated rule including recognizing that the user is not one of the known bad actors based on the comparison performed by the biometric logic, and the known bad actors including at least one of persons having a police record of criminal history or persons having a distinguishing attribute;

a filtering component to perform an action when the associated rule is violated; and an encryption logic to automatically encrypt the VoIP connection, wherein the VoIP connection is between the user and at least one other user of the VoIP system, and wherein the presence of a special signal in each user's address triggers the automatic encryption of the VoIP connection.

2. The VoIP system of claim 1, further comprising:
a voice recognition logic to recognize a voice, wherein the rule comprises a rule based on at least one of: a call originator, a call recipient, or both.

3. The VoIP system of claim 1, further comprising:
a speech recognition logic to identify words in a conversation, wherein the rule is based on a trigger word identified by a speech recognition logic.

4. The VoIP system of claim 3, wherein the trigger word comprises a series of words or a phrase.

5. The VoIP system of claim 3, wherein the trigger word comprises a plurality of weighted words, the combination of weighted words comprising the trigger word.

6. The VoIP system of claim 1, wherein the rule is based on a connection identifier.

7. The VoIP system of claim 1, wherein the biometric logic further comprises:
a fingerprint recognition logic to identify the user, and the biometric database comprises a fingerprint database utilized by the fingerprint recognition logic, and the fingerprint database including fingerprints of the known bad actors.

8. The method of claim 7, wherein the biometric database includes a face database, wherein the face database comprises images of faces of the known bad actors, and wherein the comparison of the user to the known bad actors includes comparing an image of a face of the user to the images of the faces of the known bad actors in the face database without regard to any username, telephone number, user address, Session Initiation Protocol (SIP) address, or VoIP number that is associated with the VoIP connection.

9. The VoIP system of claim 1, wherein the special signal comprises a hyper sign.

10. The VoIP system of claim 1, further comprising a dial-back system, the dial-back system including:
a security logic to generate a one-time ID and to send the one-time ID to a user's VoIP system via a PSTN;
a monitoring logic to monitor a return of the one-time ID through a network connection; and
a notification logic to notify the call control and signaling module to terminate the connection when the one-time ID is not received.

11. The method of claim 1, wherein the biometric database includes a face database, wherein the face database comprises images of faces of the known bad actors, wherein the biometric logic includes a face recognition logic, and wherein the comparison performed by the biometric logic includes the face recognition logic comparing an image of a face of the user to the images of the faces of the known bad actors in the face database without regard to any username, telephone number, user address, Session Initiation Protocol (SIP) address, or VoIP number that is associated with the VoIP connection.

12. A system to implement a secured voice-over-internet protocol (VoIP) system comprising:
a policy system to classify a VoIP connection of a user of the VoIP system;
a filtering component to determine whether the VoIP connection is of a high risk type based on the classification;
a detection and action component to detect when the high risk VoIP connection violates a rule in response to the determination that the VoIP connection is of the high risk type;
a biometric logic to compare one or more biometrics of the user to one or more biometrics in a biometric database including biometrics of known bad actors, the comparison being performed by the biometric logic in response to the determination that the VoIP connection is of the high risk type, the rule being based on a result of the comparison, and the known bad actors including at least one of persons having a police record of criminal history or persons having a distinguishing attribute;
a filtering component to perform an action when the high risk VoIP connection is determined to have violated the rule; and
an encryption logic to automatically encrypt the VoIP connection, wherein the VoIP connection is between the user and at least one other user of the VoIP system, and wherein the presence of a special signal in each user's address triggers the automatic encryption of the VoIP connection.

13. The system of claim 12, wherein the policy system classifies the VoIP connection as high risk when the VoIP connection is to a destination outside a secure zone.

14. The system of claim 12, wherein the policy system is further to classify the VoIP connection based on a risk type.

15. The system of claim 12, wherein the VoIP connection is classified based on at least one of: call originator identity, destination, voice recognition, speech recognition, or face recognition.

16. The system of claim 12, wherein the rule is based on at least one of: call originator identity, destination, voice recognition, speech recognition, length of call, or face recognition.

17. The system of claim 12, wherein the policy system monitors the VoIP connection, and alters a classification of the VoIP connection based on additional data.

18. The system of claim 12, wherein the special signal comprises a hyper sign.

19. A method of providing improved security using a voice-over-internet-protocol (VoIP) system, the method comprising:

classifying a connection risk level of a VoIP connection in response to the VoIP connection being set up for a user of the VoIP system;

when the VoIP connection is identified as a high risk VoIP connection, monitoring for a violation of a rule during the high risk VoIP connection;

when the VoIP connection is identified as the high risk VoIP connection, comparing the user, based on a biometric, to data about known bad actors in a biometric database including biometric data of the known bad actors, the comparison of the user to the known bad actors being performed without regard to any username, telephone number, user address, Session Initiation Protocol (SIP) address, or VoIP number that is associated with the high risk VoIP connection, the rule including recognizing that the user is not one of the known bad actors based on the comparison, and the known bad actors including at least one of persons having a police record of criminal history or persons having a distinguishing attribute;

performing an action in response to the violation of the rule; and triggering automatic encryption of the VoIP connection, wherein the VoIP connection is between the user and at least one other user of the VoIP system, based on the presence of a special signal in each user's address.

20. The method of claim 19, wherein classifying the connection risk level is based on monitoring a connection, and using at least one of: call originator identity, destination, voice recognition, speech recognition, length of call, or face recognition.

21. The method of claim 19, wherein the special signal comprises a hyper sign.

\* \* \* \* \*